(12) United States Patent
Itoh

(10) Patent No.: US 7,112,303 B2
(45) Date of Patent: Sep. 26, 2006

(54) SPECIMEN CENTRIFUGE APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 105 days.

(21) Appl. No.: 10/766,883

(22) Filed: Jan. 30, 2004

(65) Prior Publication Data

US 2004/0184959 A1    Sep. 23, 2004

(30) Foreign Application Priority Data

Jan. 31, 2003   (JP) .............................. 2003-024062

(51) Int. Cl.
*G01N 9/30* (2006.01)
(52) U.S. Cl. ..................... 422/72; 422/65; 436/45; 436/47; 436/48; 494/16
(58) Field of Classification Search ................ 436/43, 436/45, 47, 48; 422/72, 68.1, 63, 64, 65, 422/99, 101, 104; 494/7, 16, 20, 84
See application file for complete search history.

(56) References Cited

U.S. PATENT DOCUMENTS 5,419,871 A * 5/1995 Muszak et al. ............... 422/63
5,523,056 A * 6/1996 Miller .......................... 422/64
5,623,415 A * 4/1997 O'Bryan et al. ............ 700/225
5,769,775 A * 6/1998 Quinlan et al. ............... 494/10
5,814,276 A * 9/1998 Riggs ........................... 422/65
6,060,022 A * 5/2000 Pang et al. .................... 422/65
6,458,324 B1 * 10/2002 Schinzel ....................... 422/65
6,589,789 B1 * 7/2003 Hubert et al. ................ 436/45

FOREIGN PATENT DOCUMENTS

JP  01-189562  *  7/1989
JP  2000-84436     3/2000

* cited by examiner

*Primary Examiner*—Maureen M. Wallenhorst
(74) *Attorney, Agent, or Firm*—Nixon & Vanderhye P.C.

(57) ABSTRACT

A specimen centrifuge apparatus includes a specimen container carry-in system and a specimen container carry-out system. The specimen container carry-in system has a specimen container carry-in conveyor for loading pre-processed specimen containers into specimen centrifuge units stacked one on another in a centrifuge device, a carry-in elevator, a carry-in transfer arm, and a loading arm. The specimen container carry-out system has a specimen container carry-out conveyor for unloading the processed specimen containers from the specimen centrifuges, a carry-out elevator, a carry-out transfer arm, and an unloading arm.

5 Claims, 7 Drawing Sheets

US 7,112,303 B2

SPECIMEN CENTRIFUGE APPARATUS

CROSS-REFERENCE TO RELATED APPLICATIONS

This application is based upon and claims the benefit of priority from the prior Japanese Patent Application No. 2003-024062, filed Jan. 31, 2003, the entire contents of which are incorporated herein by reference.

BACKGROUND OF THE INVENTION

1. Field of the Invention

The invention relates to a specimen centrifuge apparatus for use in a specimen testing center and the like.

2. Description of the Related Art

The following specimen centrifuge apparatus is proposed as one for use in a specimen testing center and the like (see Japanese Patent Application KOKAI Publication No. 2000-84436). This apparatus includes first and second rotors. While one of the rotors is centrifuging a specimen, the other rotor replaces a specimen-contained tube with another one.

The above specimen centrifuge apparatus is capable of centrifuging specimens with efficiency. However, the apparatus requires a relatively large space because the first and second rotors need to be arranged together within the same horizontal surface. It is difficult for the apparatus to centrifuge a number of specimens at once because its centrifuging capacity is limited. Even though the number of specimens to be centrifuged is very small, the apparatus has to be operated in its entirety. It is therefore likely that energy will be consumed in vain.

BRIEF SUMMARY OF THE INVENTION

The invention is directed to an apparatus that substantially obviates one or more of the problems due to limitations and disadvantages of the related art.

According to an embodiment of the invention, a specimen centrifuge apparatus comprises a centrifuge device including specimen centrifuge units stacked one on another; a carry-in conveyor provided along a horizontal conveyance line that passes by the centrifuge device and having a container delivering section close to the centrifuge device, the carry-in conveyor conveying pre-processed specimen containers; a carry-out conveyor provided along the horizontal conveyance line and having a container receiving section close to the centrifuge device, the carry-out conveyor conveying processed specimen containers; a carry-in elevator provided along a vertical conveyance line that passes by the specimen centrifuge units of the centrifuge device, the carry-in elevator conveying a given number of pre-processed specimen containers from a level of the container delivering section of the carry-in conveyor to a level of the container delivering section of a designated centrifuge unit; a carry-out elevator provided along the vertical conveyance line, the carry-out elevator conveying a given number of processed specimen containers from a level of the designated centrifuge unit to a level of the container receiving section of the carry-out conveyor; a carry-in transfer arm which transfers the pre-processed specimen containers from the carry-in conveyor to the carry-in elevator; a carry-out transfer arm which transfers the processed specimen containers from the carry-out elevator to the carry-out conveyor; a loading arm attached to each of the specimen centrifuge units, the loading arm removing the pre-processed specimen containers from the carry-in elevator and loads the pre-processed specimen containers into one of the specimen centrifuge units; and an unloading arm attached to each of the specimen centrifuge units, the unloading arm unloading the processed specimen containers from one of the specimen centrifuge units and moving the processed specimen containers to the carry-out elevator.

Additional objects and advantages of the invention will be set forth in the description which follows, and in part will be obvious from the description, or may be learned by practice of the invention.

The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention and, together with the general description given above and the detailed description of the embodiments given below, serve to explain the principles of the invention in which.

DETAILED DESCRIPTION OF THE INVENTION (First Embodiment)

As shown in FIGS. 1 to 4, a specimen centrifuge apparatus according to a first embodiment of the invention comprises a centrifuge device 10 including a plurality of specimen centrifuge units 11 and 12 (two in the first embodiment). The specimen centrifuge units 11 and 12 are stacked one on another.

Figure 4:
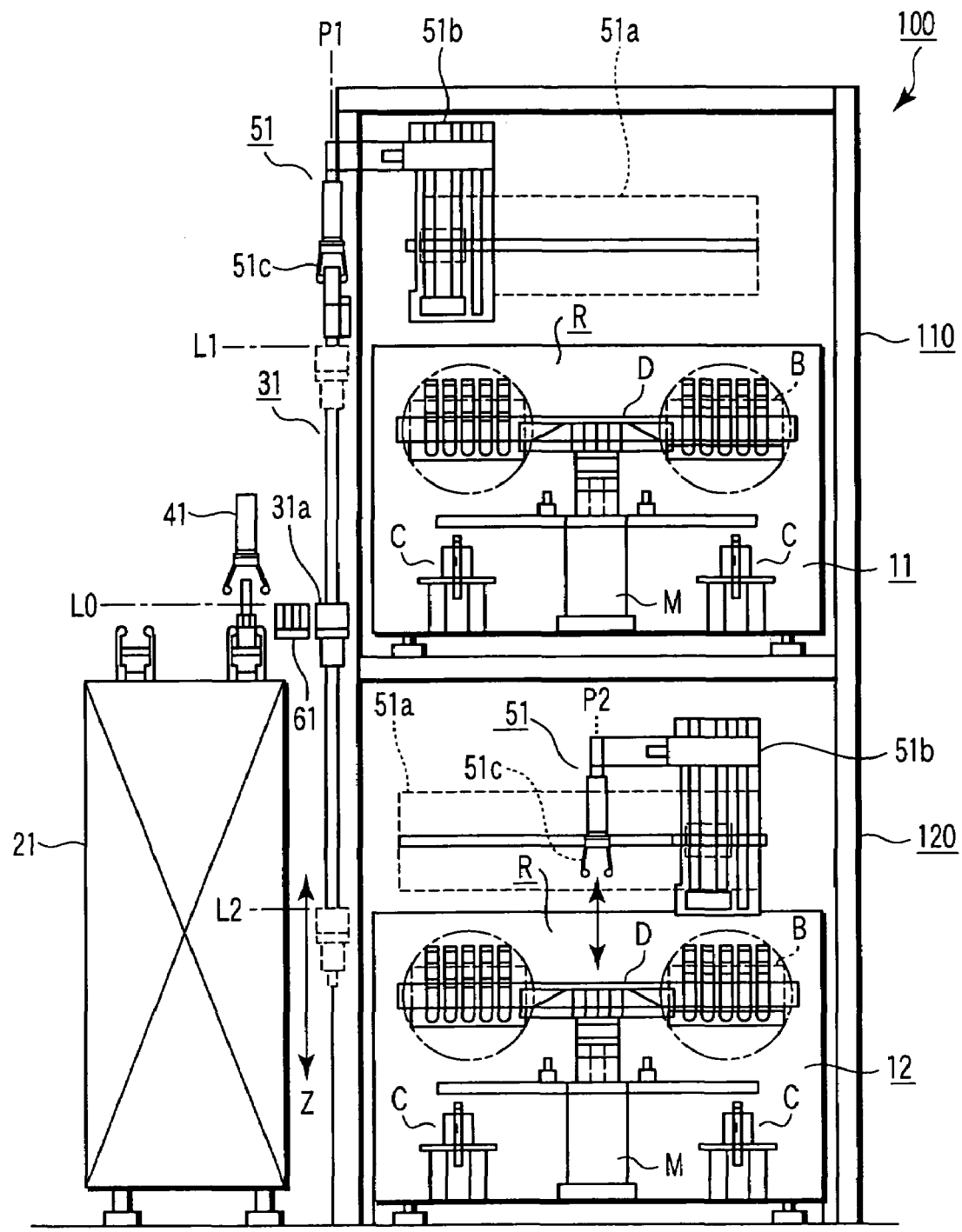
FIG. 4 is a longitudinal sectional view taken along line IV—IV of FIG. 2 and showing a configuration of the specimen centrifuge apparatus according to the first embodiment of the invention.

The specimen centrifuge units 11 and 12 are stored in their respective first and second cabinets 110 and 120, as shown in FIG. 4. The cabinets 110 and 120 are formed by vertically partitioning a rectangular parallelepiped housing 100 into two.

Each of the, specimen centrifuge units 11 and 12 has a motor M, a rotor R and a position sensor C. The motor M is set up on the floor of the corresponding one of the cabinets 110 and 120. The rotor R is rotated by the motor M. The position sensor C senses a position of the rotation of the rotor R and positions the rotor R to easily load and unload specimen containers, which will be described later.

The rotor R has a plurality of specimen-container buckets B. The buckets B are shakably attached to the circumference of a rotating disc D of the rotor R. Each of the buckets B can store a given number of (five in the first embodiment) specimen containers 1. The rotor R will be described in detail later.

Each of the cabinets 110 and 120 has an opening (not shown) on its front wall. The specimen containers 1 can be inserted and removed through the opening.

A carry-in conveyor 21 is provided along a horizontal conveyance line HL1 that passes by the centrifuge device 10. The carry-in conveyor 21 conveys a plurality of pre-processed specimen containers 1 and has a belt-type conveyance lane formed to make a U-turn portion near the centrifuge device 10. The U-turn portion of the belt-type conveyance lane, which is close to the centrifuge device 10, has a container delivering section 21a. Thus, the specimen containers 1 such as test tubes are held by a holder 2 called a columnar rack and conveyed in the horizontal direction as indicated by arrow X1 in FIG. 3.

A carry-out conveyor 22 is provided along a horizontal conveyance line HL2 that passes by the centrifuge device 10. In the first embodiment, the horizontal conveyance line HL2 is aligned with the horizontal conveyance line HL1. The carry-out conveyor 22 conveys a plurality of processed specimen containers 1' and has a belt-type conveyance lane formed to make a U-turn portion near the centrifuge device 10. The U-turn portion of the belt-type conveyance lane, which is close to the centrifuge device 10, has a container receiving section 22a. Thus, the processed specimen containers 1' such as test tubes are held by the holder 2 and conveyed in the horizontal direction as indicated by arrow X2 in FIG. 3.

Figure 1:
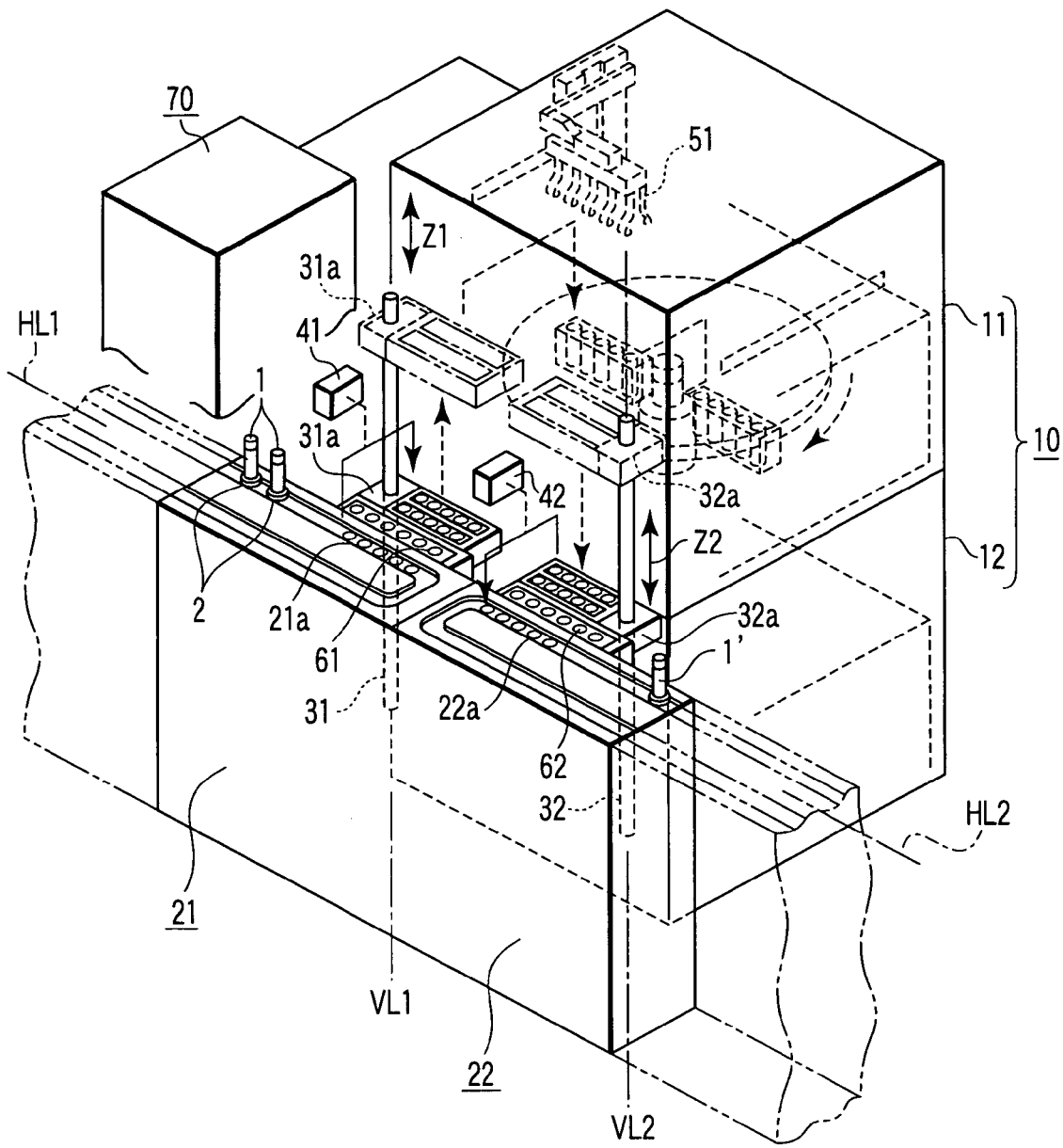
FIG. 1 is a schematic perspective view of a specimen centrifuge apparatus according to a first embodiment of the invention.
Figure 2:
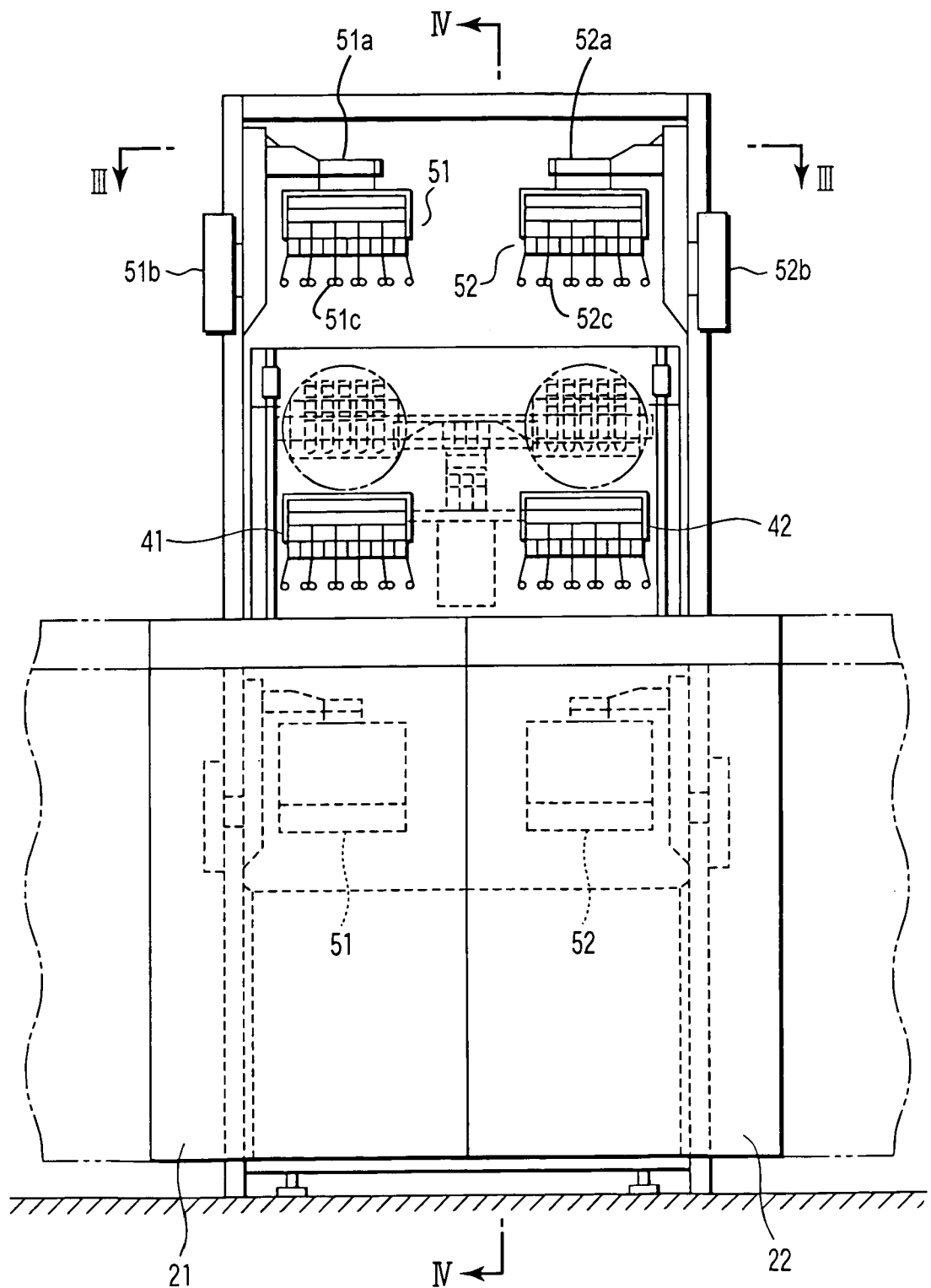
FIG. 2 is a partly cutaway front view of the specimen centrifuge apparatus according to the first embodiment of the invention.

A carry-in elevator 31 is provided in front of the centrifuge device 10 along a vertical conveyance line VL1 that passes by the specimen centrifuge units 11 and 12, as illustrated in FIG. 1. The carry-in elevator 31 includes a specimen container rack 31a that stores a given number of (ten in this embodiment) pre-processed specimen containers 1. Thus, the carry-in elevator 31 can convey the pre-processed specimen containers 1, which are stored in the specimen container rack 31a, from level L0 of the container delivering section 21a of the carry-in conveyor 21 to level L1 or L2 of a designated one of the centrifuge units 11 and 12, as indicated by double-headed arrow Z1 in FIG. 1.

A carry-out elevator 32 is provided in front of the centrifuge device 10 along a vertical conveyance line VL2 that passes by the centrifuge units 11 and 12, as illustrated in FIG. 1. The carry-out elevator 32 includes a specimen container rack 32a that stores a given number of (ten in this embodiment) processed specimen containers 1'. Thus, the carry-out elevator 32 can convey the processed specimen containers 1', which are stored in the specimen container rack 32a, from level L0 of the container receiving section 22a of the carry-out conveyor 22 to level L1 or L2 of a designated one of the centrifuge units 11 and 12, as indicated by double-headed arrow Z2 in FIG. 1.

The carry-in and carry-out elevators 31 and 32 are exactly driven by a controller 70 such that their specimen container racks 31a and 32a can be opposed to the openings of the specimen centrifuge units 11 and 12, respectively.

A carry-in transfer arm (robot arm) 41 transfers the pre-processed specimen containers 1 from the carry-in conveyor 21 to the carry-in elevator 31. A carry-out transfer arm (robot arm) 42 transfers a processed specimen containers 1' from the carry-out elevator 32 to the carry-out conveyor 22.

The specimen centrifuge units 11 and 12 each have a loading arm 51. The loading arm 51 removes a pre-processed specimen container 1 from the carry-in elevator 31 and loads it into one of the specimen centrifuge units 11 and 12. In other words, the loading arm 51 can be slid in the horizontal direction between positions P1 and P2 by a horizontal slide mechanism 51a. It also can be slid in the vertical direction between positions P1 and P2 by a vertical slide mechanism 51b. The loading arm 51 has a hand portion 51c at its end. The pre-processed specimen containers 1 can be caught by and released from the hand portion 51c.

The specimen centrifuge units 11 and 12 each have an unloading arm 52. The unloading arm 52 unloads a processed specimen container 1' from one of the specimen centrifuge units 11 and 12 and moves it to the carry-out elevator 32. In other words, the unloading arm 52 can be slid in the horizontal direction between positions P1 and P2 by a horizontal slide mechanism 52a. It also can be slid in the vertical direction between positions P1 and P2 by a vertical slide mechanism 52b. The unloading arm 52 has a hand portion 52c at its end. The pre-processed specimen containers 1' can be caught by and released from the hand section 52c. Reference numerals 61 and 62 denote a carry-in dummy rack and a carry-out dummy rack, respectively.

The specimen centrifuge units 11 and 12 can be operated independently. The controller 70 can control the specimen centrifuge units 11 and 12 simultaneously or selectively. The controller 70 can also control them such that the rotation direction of the rotor R of each centrifuge unit can be set in a given direction.

Figure 5:
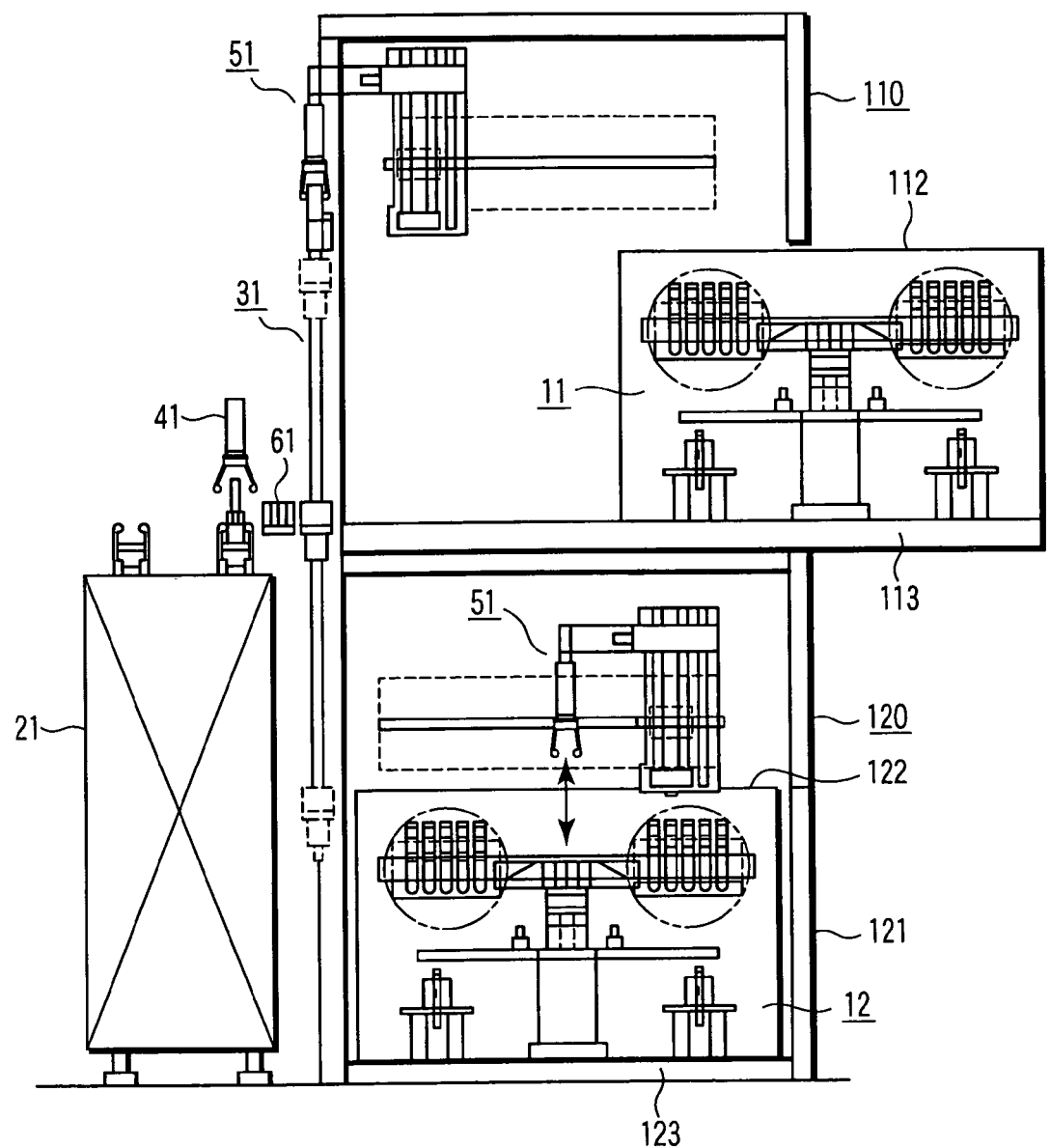
FIG. 5 is a sectional view corresponding to FIG. 4 and showing the specimen centrifuge apparatus according to the first embodiment of the invention, which is under maintenance.

FIG. 5 is a sectional view corresponding to FIG. 4 and showing the specimen centrifuge apparatus under maintenance. Referring to FIG. 5, the specimen centrifuge units 11 and 12 are insertably and removably stored in their respective cabinets 110 and 120 stacked one on another. More specifically, the rear walls of the cabinets 110 and 120 serve as lids 111 (not shown) and 121 that can freely be opened and closed. Inner boxes 112 and 122 containing their respective specimen centrifuge units 11 and 12 can be slid into and out of the cabinets 110 and 120 in the horizontal direction by slide rails 113 and 123, respectively. When the need arises, the specimen centrifuge units 11 and 12 can be drawn out as shown and subjected to given maintenance.

Figure 6A:
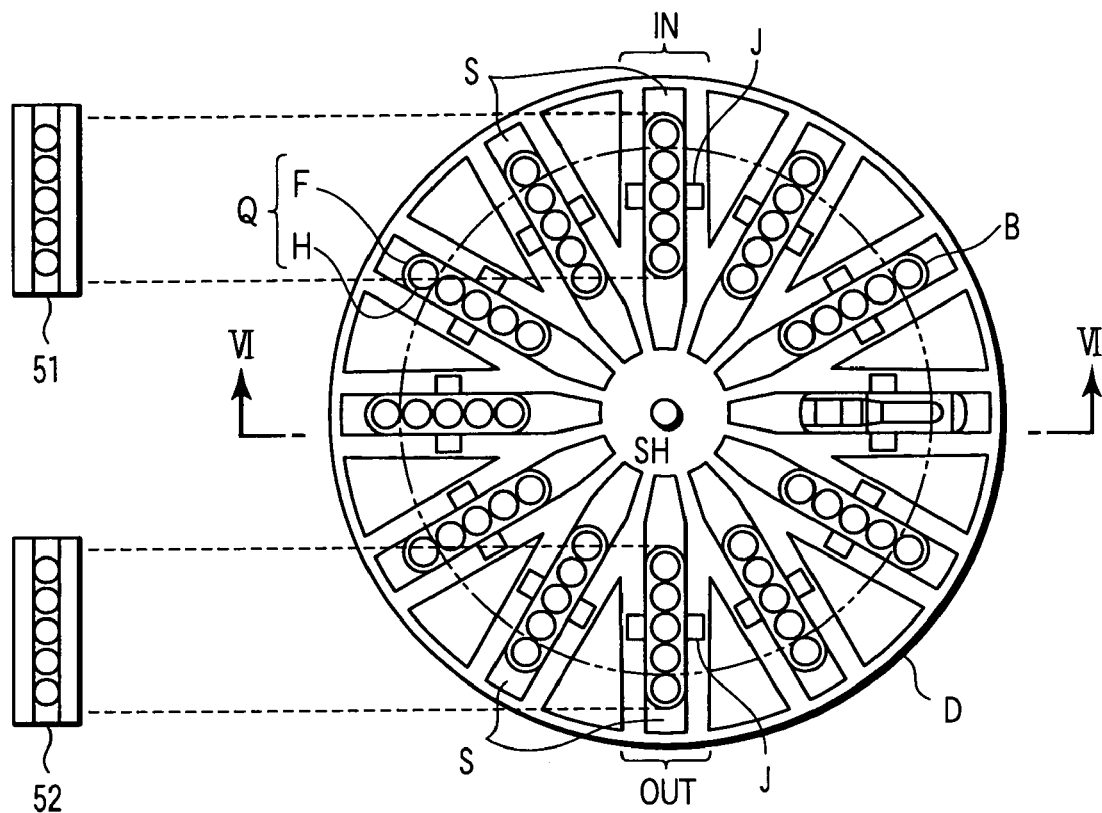
FIG. 6A is a top view of a rotor of the specimen centrifuge apparatus according to the first embodiment of the invention.
Figure 6B:
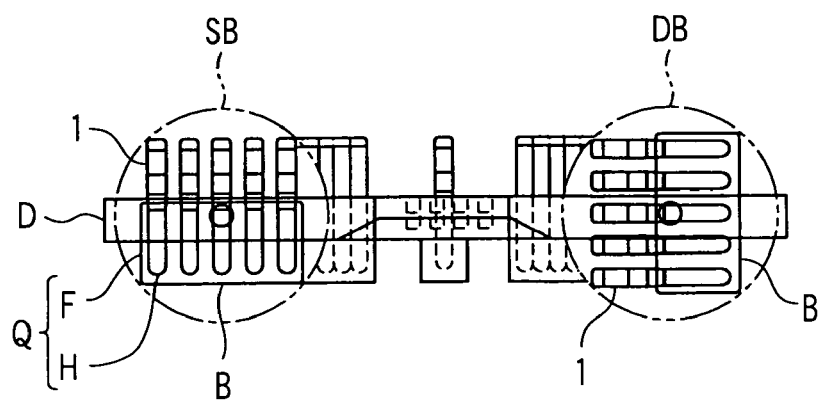
FIG. 6B is a sectional view taken along line VI—VI of FIG. 6A.

Referring to FIGS. 6A and 6B, the rotor R has a rotating disc D that can rotate at high speed at the time of centrifuging. The controller 70 can set the rotating position of the rotating disc D at a given angle when the pre-processed specimen containers 1 are carried in and the processed specimen containers 1' are carried out. A plurality of rectangular slots S are arranged radially from the rotation axis SH on the rotating disc D. A hollow, rectangular parallelepiped specimen container bucket B is shakably mounted in each of the slots S. In other words, the bucket B is supported at its middle part in its corresponding slot S through the rotation shaft J. If, therefore, the rotation disc D rotates at high speed, the bottom of each bucket B is swung up in the radial direction of the disc D by centrifugal force. Each bucket B includes a container storing section Q. The container storing section Q has a hollow, rectangular parallelepiped frame F in which a plurality of (five in the first embodiment) tube-type container holders H are attached such that the specimen containers 1 can be arranged in line. In FIG. 6A, IN indicates a position in which a container is inserted and OUT denotes a position in which a container is removed.

An operation of the specimen centrifuge apparatus according to the embodiment will now be described.

The pre-processed specimen containers 1 each containing a specimen to be centrifuged are held in the holder 2 and conveyed to the proximity of the centrifuge device 10 by the carry-in conveyor 21. The containers 1 stop when they reach the container delivering section 21a on the conveyance lane of the carry-in conveyor 21. The stopped containers 1 are removed five by five by the carry-in transfer arm 41 and arranged in two lines in the specimen container rack 31a attached to the carry-in elevator 31.

When the number of specimen containers 1 arranged in two lines in the specimen container rack 31 does not reach the prescribed number, or when the specimen containers 1 are not arranged five by five, a required number of dummy specimen containers, which are stocked in advance in the carry-in dummy rack 61, are removed and inserted in empty space of the rack 31a.

The carry-in elevator 31 conveys the ten specimen containers 1 arranged in the specimen container rack 31a to one of the specimen centrifuge units 11 and 12, which is designated by a host computer (not shown), for example, the specimen centrifuge unit 11 in the upper stage shown in FIG. 4.

The specimen containers 1 conveyed to the upper specimen centrifuge unit 11 are sequentially carried into the centrifuge unit 11 by the carry-in arm 51 attached to the centrifuge device 10 and then loaded into the specimen container bucket B.

More specifically, five specimen containers 1 in the first line in the specimen container rack 31a are caught by a hand section 51c of the carry-in arm 51 and removed therefrom as a vertical slide mechanism 51b goes up. The specimen containers 1 raised up to the upper limit by the vertical slide mechanism 51b are slid from position P1 to position P2 by a horizontal slide mechanism 51a. When the vertical slide mechanism 51b goes down, the specimen containers 1 are inserted into the specimen container bucket B set in the container inserting position IN (corresponding to position P2) of the rotor R. The hand section 51c opens and thus the five specimen containers 1 are loaded into the specimen container bucket B.

Like the specimen containers 1 in the first line, five specimen containers 1 in the second line in the specimen container rack 31a are loaded into the specimen container bucket B by a series of operations of the carry-in arm 51. The specimen container bucket B for the containers 1 in the second line is located on the rotor R 180 degrees differently from that for the containers 1 in the first line.

In other words, the rotor of the centrifuge unit 11 rotates 180 degrees while the carry-in arm 51 is moving to catch the specimen containers 1 in the second line after the carry-in operation of the specimen containers 1 in the first line is completed. Thus, the specimen container bucket B, which is originally located in the position (corresponding to the container removing position OUT) which is 180 degrees different from the container inserting position IN, is set in the container inserting position IN. The specimen containers 1 in the second line are therefore inserted into the specimen container bucket B set in the container inserting position IN by the carry-in arm 51.

Repeating the above operation while varying the rotation angle of the rotor R slot by slot, the loading of specimen containers 1 into each bucket B of the rotor R of the specimen centrifuge unit 11 is completed. Then, the specimen centrifuge unit 11 starts to rotate to perform a centrifuge operation.

When the centrifuge operation is performed, each specimen container bucket B shifts from the state indicated by symbol SB to that indicated by symbol DB in FIG. 6B. In other words, the bottom of the bucket B is swung up approximately 90 degrees in the radial direction from the axis of the rotating disc D. At this time, the axes of all the specimen containers 1 in the specimen container bucket B become parallel to the radial direction of the disc D, and the centrifugal force is exerted in the axial direction of the specimen containers 1. When, for example, blood is centrifuged, the separation surface between serum and clot is at right angles to the axis of each specimen container 1. Therefore, when an automated dispensing apparatus sucks up serum, there is not much fear that the serum remains.

Figure 3:
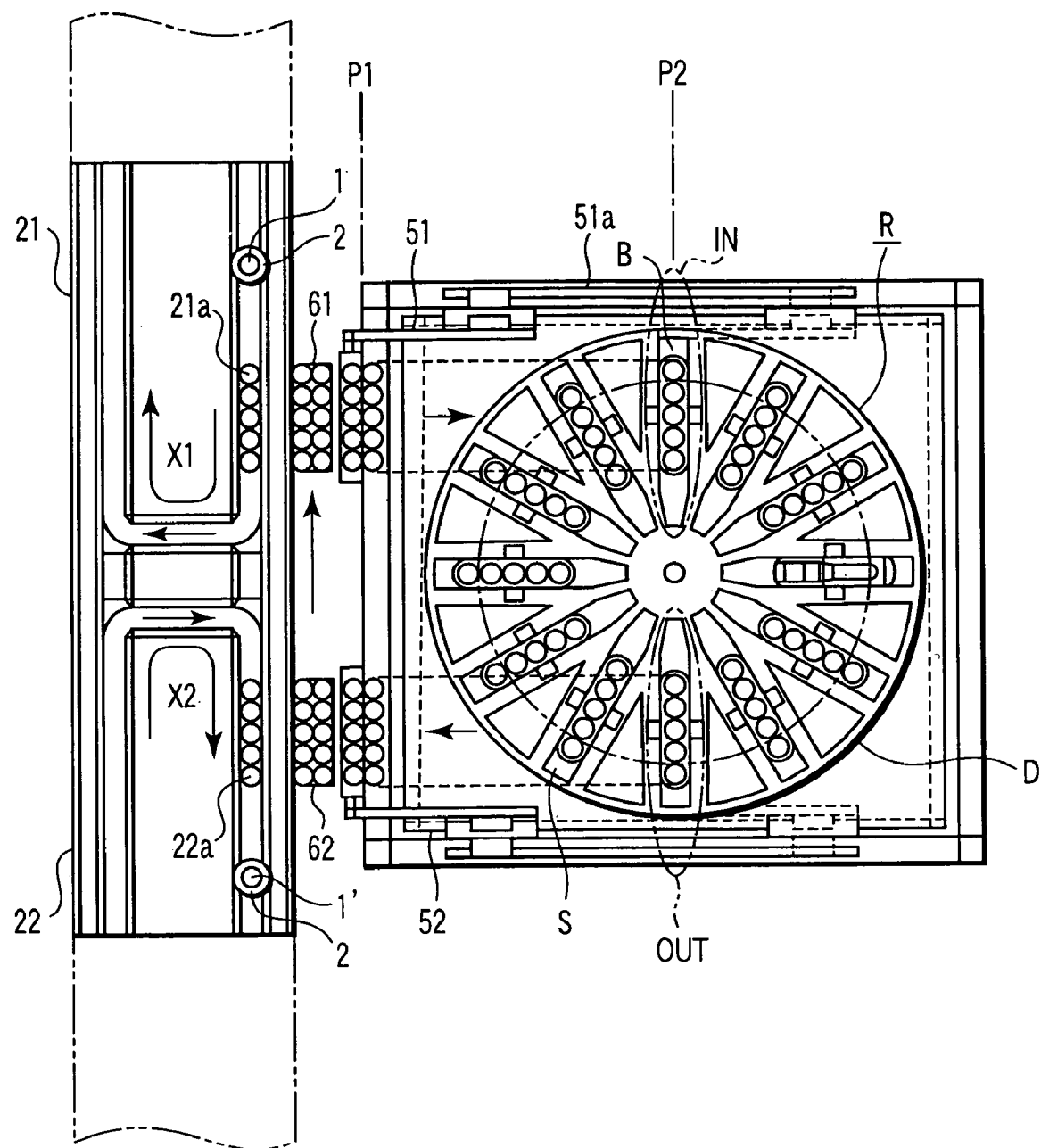
FIG. 3 is a cross-sectional view taken along line III—III of FIG. 2 and showing a configuration of the specimen centrifuge apparatus according to the first embodiment of the invention.

When the centrifuge operation is completed by the specimen centrifuge unit 11, the carry-out arm 52 sequentially removes the processed specimen containers 1', the specimens of which are centrifuged in the specimen container bucket B located in the container removing position OUT of the rotor R corresponding to the position P2, in the order opposite to that of the above specimen container loading operation. Then, they are moved to the specimen container rack 32a attached to the carry-out elevator 32. The processed specimen containers 1' are conveyed to level L0 of the container receiving section 22a of the carry-out conveyor 21 by the carry-out elevator 32. The processed specimen containers 1' are then moved to the specimen container holder 2 of the carry-out conveyor 22 by the carry-out transfer arm 42. The dummy specimen containers are stored in the carry-out dummy rack 62 as shown in FIG. 3. After that, they are returned to the carry-in dummy rack 61.

The above operation is repeated while varying the rotation angle of the rotor R slot by slot. As a result, all the specimen containers 1' whose specimens are centrifuged by the specimen centrifuge unit 11 are moved to the specimen container holder 2 of the carry-out conveyor 22. The moved specimen containers 1' are carried out by the carry-out conveyor 22. The one-cycle specimen centrifuge operation using the specimen centrifuge unit 11 is therefore completed.

The specimen centrifuge unit 12 in the lower stage performs the same operation as that of the specimen centrifuge unit 11 in the upper stage. The operation of carrying in the specimen containers 1 whose specimens are to be centrifuged by the centrifuge unit 12 can be performed any time during a period of time except when the operation of carrying in the specimen containers 1 whose specimens are to be centrifuged by the centrifuge unit 11 is carried out.

The controller 70 drives the specimen centrifuge units 11 and 12 at the same time or drives a selected one of them.

The centrifuge operation of each of the centrifuge units 11 and 12 is performed for about five minutes at preset rotation speed (which is set such that the gravitational acceleration applied to the specimen containers 1 loaded into the rotating disc D having a given diameter becomes 2000 G).

The time required for loading/unloading the specimen containers into/from one specimen centrifuge unit is about two minutes and thirty seconds including the time required for positioning the rotor of the specimen centrifuge. Adding five minutes for the centrifuge operation to the above time, the total time required for performing the centrifuge operation once by one specimen centrifuge unit is about seven minutes and thirty seconds. It is thus possible to perform the centrifuge operation eight times per hour. Consequently, the number of specimen containers to be processed per hour by one specimen centrifuge unit is 480 (=60×8). Since two specimen centrifuge units 11 and 12 are stacked one on another in the first embodiment, the total number of specimen containers to be processed (centrifuging capacity) per hour is 960 (=480×2).

When specimen container units are carried out of one of the specimen centrifuge units, e.g., the centrifuge unit 11, specimen containers 1 can quickly start to be carried into the other specimen centrifuge unit, e.g., the centrifuge unit 12. Accordingly, waiting time is greatly shortened.

The first embodiment can provide a specimen centrifuge apparatus having the following advantages.

1) The system has a large centrifuging capacity.
2) The space for the system is small.
3) Whether the number of specimens to be centrifuged is small or large, they can be centrifuged with efficiency.
4) Since waiting time for carrying in/carrying out specimen containers is short, a centrifuge operation can be performed quickly.

According to an aspect of the first embodiment, there is provided a specimen centrifuge apparatus comprising a centrifuge device including a plurality of specimen centrifuge units stacked one on another; a carry-in conveyor provided along a horizontal conveyance line that passes by the centrifuge device and having a container delivering section close to the centrifuge device, the carry-in conveyor conveying a plurality of pre-processed specimen containers; a carry-out conveyor provided along a horizontal conveyance line that passes by the centrifuge device and having a container receiving section close to the centrifuge device, the carry-out conveyor conveying a plurality of processed specimen containers; a carry-in elevator provided along a vertical conveyance line VL1 that passes by the specimen centrifuge units of the centrifuge device, the carry-in elevator conveying a given number of pre-processed specimen containers from a level of the container delivering section of the carry-in conveyor to a level of a designated centrifuge unit; a carry-out elevator provided along a vertical conveyance line that passes by the specimen centrifuge units of the centrifuge device, the carry-out elevator conveying a given number of processed specimen containers from a level of a designated centrifuge unit to a level of the container receiving section of the carry-out conveyor; a carry-in transfer arm which transfers the pre-processed specimen containers from the carry-in conveyor to the carry-in elevator; a carry-out transfer arm which transfers the processed specimen containers from the carry-out elevator to the carry-out conveyor; a loading arm attached to each of the specimen centrifuge units, the loading arm removing the pre-processed specimen containers from the carry-in elevator and loads the pre-processed specimen containers into one of the specimen centrifuge units; and an unloading arm attached to each of the specimen centrifuge units, the unloading arm unloading the processed specimen containers from one of the specimen centrifuge units and moving the processed specimen containers to the carry-out elevator.

Other embodiments of the specimen centrifuge apparatus according to the invention will be described. The same portions as those of the first embodiment will be indicated in the same reference numerals and their detailed description will be omitted.

(Second Embodiment)

Figure 7:
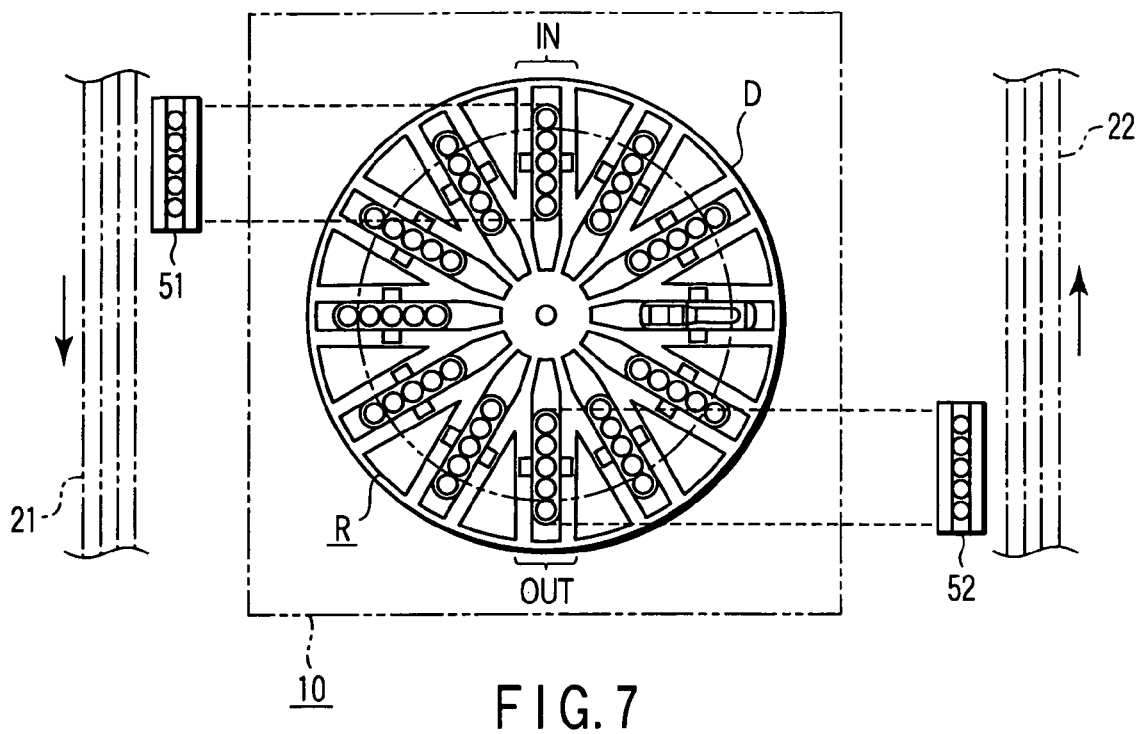
FIG. 7 is a top view of the principal part of a specimen centrifuge apparatus according to a second embodiment of the invention.

FIG. 7 is a top view of the principal part of a specimen centrifuge apparatus according to a second embodiment of the invention.

The second embodiment differs from the first embodiment as follows. The carry-in conveyor 21 and carry-out conveyor 22 are arranged in parallel to each other and the centrifuge device 10 is interposed between the conveyors 21 and 22. The locations of container inserting position IN and container removing position OUT on the rotor R are 180 degrees different from each other.

The second embodiment has the advantage that the conveyance lanes of the carry-in conveyor 21 and carry-out conveyor 22 each have only to be formed straightly. Since the second embodiment is the same as the first embodiment except for the above, its detailed descriptions are omitted.

(Third Embodiment)

Figure 8:
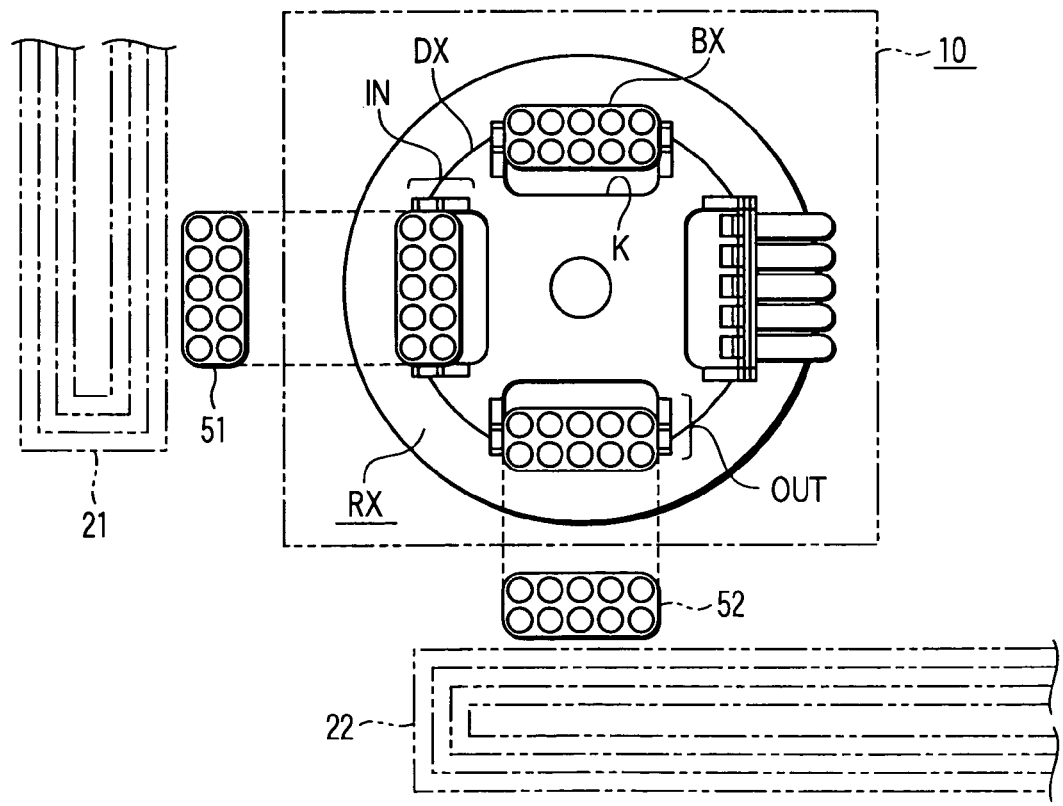
FIG. 8 is a top view of the principal part of a specimen centrifuge apparatus according to a third embodiment of the invention.

FIG. 8 is a top view of the principal part of a specimen centrifuge apparatus according to a third embodiment of the invention.

The third embodiment differs from the first embodiment as follows. A plurality of (four in the third embodiment) notches K are formed in the circumference of rotating disc DX of rotor RX of centrifuge device 10. Four specimen container buckets BX each shaped like a rectangular parallelepiped are arranged in their respective notches K such that the longitudinal direction of each bucket BX is set toward the tangent to the rotating disc DX.

The third embodiment also differs from the first embodiment as follows. The locations of carry-in and carry-out conveyors 21 and 22 are 90 degrees different from each other, and the specimen containers are inserted at and removed from the container inserting and removing positions IN and OUT which are spaced by 90 degrees on the rotor RX.

The invention can be applied to a centrifuge device including a rotor RX, which is configured as shown in FIG. 8 as the third embodiment. Since the third embodiment is the same as the first embodiment except for the above, its detailed descriptions are omitted.

(Features of the Embodiments)

[1] A specimen centrifuge apparatus according to an embodiment of the invention comprises:

a centrifuge device 10 including a plurality of (two in the embodiment) specimen centrifuge units 11 and 12 stacked one on another;

a carry-in conveyor 21 provided along a horizontal conveyance line HL1 that passes by the centrifuge device 10 and having a container delivering section 21a close to the centrifuge device 10, the carry-in conveyor 21 conveying a plurality of pre-processed specimen containers 1;

a carry-out conveyor 22 provided along a horizontal conveyance line HL2 that passes by the centrifuge device 10 and having a container receiving section 22a close to the centrifuge device 10, the carry-out conveyor 22 conveying a plurality of processed specimen containers 1';

a carry-in elevator 31 provided along a vertical conveyance line VL1 that passes by the specimen centrifuge units 11 and 12 of the centrifuge device 10, the carry-in elevator 31 conveying a given number of (ten in the embodiment) pre-processed specimen containers 1 from a level L0 of the container delivering section 21a of the carry-in conveyor 21 to one of levels L1 and L2 which corresponds to a designated one of the centrifuge units 11 and 12;

a carry-out elevator 32 provided along a vertical conveyance line VL2 that passes by the specimen centrifuge units 11 and 12 of the centrifuge device 10, the carry-out elevator 32 conveying a given number of (ten in the embodiment) processed specimen containers 1' from one of levels L1 and L2 which corresponds to a designated one of the centrifuge units 11 and 12 to a level L0 of the container receiving section 22a of the carry-out conveyor 22;

a carry-in transfer arm 41 which transfers the pre-processed specimen containers 1 from the carry-in conveyor 21 to the carry-in elevator 31;

a carry-out transfer arm 42 which transfers the processed specimen containers 1' from the carry-out elevator 32 to the carry-out conveyor 22;

a loading arm 51 attached to each of the specimen centrifuge units 11 and 12, the loading arm 51 removing the pre-processed specimen containers 1 from the carry-in elevator 31 and loads the pre-processed specimen containers 1 into one of the specimen centrifuge units 11 and 12; and an unloading arm 52 attached to each of the specimen centrifuge units 11 and 12, the unloading arm 52 unloading the processed specimen containers 1' from one of the specimen centrifuge units 11 and 12 and moving the processed specimen containers 1' to the carry-out elevator 32.

The above-described specimen centrifuge apparatus comprises a centrifuge device 10 including a plurality of (two in the present embodiment) specimen centrifuge units 11 and 12 stacked one on another. A large centrifuging capacity corresponding to the total number of specimen centrifuge units 11 and 12 can be achieved. The space for one specimen centrifuge unit is enough for the two specimen centrifuge units 11 and 12 and thus the setup space for the centrifuge units 11 and 12 can be minimized. The conveyor, transfer arm, elevator, and loading/unloading arm are provided on each of the carry-in and carry-out sides. Thus, the carry-in operation in one of the specimen centrifuge units (e.g., centrifuge unit 11) and the carry-out operation in the other specimen centrifuge unit (e.g., centrifuge unit 12) can be performed independently of each other. Consequently, a very efficient centrifuge operation can be performed.

[2] In the specimen centrifuge apparatus according to the above item [1], a container delivering section 21a of the carry-in conveyor 21 is arranged in parallel to a specimen container rack 31a attached to the carry-in elevator 31 and a rectangular parallelepiped specimen container bucket B located in a container inserting section IN of a rotor R of each of the specimen centrifuge units 11 and 12 to allow the pre-processed specimen containers 1 arranged in line to move, and the container receiving section 22a of the carry-out conveyor 22 is arranged in parallel to a specimen container rack 32a attached to the carry-out elevator 32 and a rectangular parallelepiped specimen container bucket B located in a container removing section OUT of the rotor R of each of the specimen centrifuge units 11 and 12 to allow the processed specimen containers 1' arranged in line to move.

In the foregoing specimen centrifuge apparatus, the carry-in transfer arm 41 and the loading arm 51 of each of the specimen centrifuge units 11 and 12 have only to move the pre-processed specimen containers 1 in parallel, and the carry-out transfer arm 42 and the unloading arm 52 of each of the specimen centrifuge units 11 and 12 have only to move the processed specimen containers 1' in parallel. In other words, none of these arms require any complicated movement such as rotation and thus the moving mechanism of the arms can be simplified.

[3] In the specimen centrifuge apparatus according to the above item [2], the rotor R of each of the specimen centrifuge units 11 and 12 is located such that a longitudinal direction of the rectangular parallelepiped specimen container bucket B corresponds to the radial direction of a rotating disc D.

In the foregoing specimen centrifuge apparatus, the specimen container bucket B, which is located in the container inserting section IN of each of the specimen centrifuge units 11 and 12, is easily provided in parallel to the specimen container rack 31a of the carry-in elevator 31. Further, the specimen container bucket B, which is located in the container removing section OUT of each of the specimen centrifuge units 11 and 12, is easily provided in parallel to the specimen container rack 32a of the carry-out elevator 32.

[4] In the specimen centrifuge apparatus according to one of the above items [1], [2] and [3], the specimen centrifuge units 11 and 12 are operated independently and controlled simultaneously or selectively by a controller 70.

In the above specimen centrifuge apparatus, the specimen centrifuge units 11 and 12 can selectively be operated. Thus, the minimum specimen centrifuge unit has only to be operated in accordance with the number of specimen containers 1 conveyed by the conveyor 21, with the result that the centrifuge operation can be performed with efficiency.

[5] In the specimen centrifuge apparatus according to one of the above items [1], [2] and [3], each of the specimen centrifuge units 11 and 12 has a rotor R whose rotation direction is set in a given direction by the controller 70.

In the foregoing specimen centrifuge apparatus, for example, the rotation directions of rotors R can be opposed alternately. If so, the mechanical vibrations of the specimen centrifuge units 11 and 12 interfere with each other. Noise is therefore decreased and the lifetime of the specimen centrifuge units 11 and 12 can be lengthened.

[6] In the specimen centrifuge apparatus according to one of the above items [1], [2] and [3], the specimen centrifuge units 11 and 12 are insertably and removably stored in respective cabinets 110 and 120 stacked one on another.

In the above-described specimen centrifuge apparatus, the specimen centrifuge units 11 and 12 can be drawn out of the cabinets 110 and 120 one by one. Thus, the maintenance of the specimen centrifuge units 11 and 12 can easily be performed.

While the description above refers to particular embodiments of the invention, it will be understood that many modifications may be made without departing from the spirit thereof. The accompanying claims are intended to cover such modifications as would fall within the true scope and spirit of the invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein. For example, three or more specimen centrifuges can be stacked one on another.

What is claimed is:

1. A specimen centrifuge apparatus comprising:
   a centrifuge device including specimen centrifuge units stacked one on another;
   a carry-in conveyor which horizontally conveys pre-processed specimen containers;
   a carry-out conveyor which horizontally conveys processed specimen containers;
   a carry-in elevator which is provided at a side of the centrifuge units and vertically conveys a given number of pre-processed specimen containers from a container delivering section of the carry-in conveyor to a container delivering section of one of the centrifuge units;

a carry-out elevator which is provided at a side of the centrifuge units and vertically conveys a given number of processed specimen containers from the one of the centrifuge units to a container receiving section of the carry-out conveyor;

a loading arm attached to each of the specimen centrifuge units, the loading arm removing the pre-processed specimen containers from the carry-in elevator and loading the pre-processed specimen containers into one of the specimen centrifuge units; and an unloading arm attached to each of the specimen centrifuge units, the unloading arm unloading the processed specimen containers from one of the specimen centrifuge units and moving the processed specimen containers to the carry-out elevator.

2. The specimen centrifuge apparatus according to claim 1, wherein the container delivering section of the carry-in conveyor is arranged in parallel to both a specimen container rack which is attached to the carry-in elevator and a rectangular parallelepiped specimen container bucket located in a container inserting section of a rotor of each of the specimen centrifuge units to allow the pre-processed specimen containers arranged in line to move, and the container receiving section of the carry-out conveyor is arranged in parallel to both a specimen container rack which is attached to the carry-out elevator and a rectangular parallelepiped specimen container bucket located in a container removing section of the rotor of each of the specimen centrifuge units to allow the processed specimen containers arranged in line to move.

3. The specimen centrifuge apparatus according to claim 2, wherein the rotor of each of the specimen centrifuge units is located such that a longitudinal direction of the rectangular parallelepiped specimen container bucket corresponds to the radial direction of a rotating disc.

4. The specimen centrifuge apparatus according to claim 1, further comprising a controller which operates the specimen centrifuge units simultaneously or selectively.

5. The specimen centrifuge apparatus according to claim 1, further comprising a controller which sets rotation directions of a rotor of the specimen centrifuge units in a given direction.

* * * * *